United States Patent [19]

Bonse et al.

[11] 4,370,498

[45] Jan. 25, 1983

[54] PREPARATION OF α-KETOCARBOXYLIC ACID N-ACYLAMIDES

[75] Inventors: Gerhard Bonse, Cologne; Heinz U. Blank, Odenthal, both of Fed. Rep. of Germany

[73] Assignee: Bayer Aktiengesellschaft, Leverkusen, Fed. Rep. of Germany

[21] Appl. No.: 235,497

[22] Filed: Feb. 19, 1981

[30] Foreign Application Priority Data

Mar. 8, 1980 [DE] Fed. Rep. of Germany ....... 3009044

[51] Int. Cl.³ ............... C07C 102/08; C07C 103/147; C07C 103/19; C07C 103/24

[52] U.S. Cl. ................................... 564/155; 564/153; 564/159; 560/37; 560/125; 560/170; 260/404; 260/465 D; 544/168; 546/226; 548/128; 548/215; 548/240; 548/255; 548/343; 548/346; 548/378; 548/540; 549/496

[58] Field of Search ...................... 564/153, 155, 159; 260/404, 465 D, 326.73, 347.3; 560/37, 125, 170; 544/168; 546/226; 548/128, 215, 240, 255, 343, 346, 378

[56] References Cited

U.S. PATENT DOCUMENTS 4,175,188 11/1979 Klenk .................................. 544/182

FOREIGN PATENT DOCUMENTS 2705048 8/1977 Fed. Rep. of Germany .

OTHER PUBLICATIONS

Shaw et al., CA 49:3979(b), 1955.

Patai, *Amides*, pp. 121, 338–339, Zabicky, ed., Interscience (1970).

*Primary Examiner*—Thomas A. Waltz
*Attorney, Agent, or Firm*—Sprung, Horn, Kramer & Woods

[57] ABSTRACT

α-Ketocarboxylic acid N-acylamides of the formula $$R^1-CO-CO-NH-CO-R^2$$

in which
  $R^1$ is an optionally substituted aliphatic radical with up to 12 carbon atoms, an optionally substituted cycloalkyl radical with 3 to 10 carbon atoms, an optionally substituted heterocyclic radical, and
  $R^2$ is an optionally substituted aliphatic radical with up to 8 carbon atoms or an optionally substituted phenyl radical, are prepared by reacting an acyl cyanide of the formula $$R^1-CO-CN$$

with a carboxylic acid anhydride of the formula $$R^2-CO-O-CO-R^2$$

in the presence of a strong acid, and then adding water to the reaction mixture. The products can be used directly in the synthesis of known herbicides.

15 Claims, No Drawings

PREPARATION OF α-KETOCARBOXYLIC ACID N-ACYLAMIDES

The present invention relates to certain new α-ketocarboxylic acid N-acylamides, to an unobvious process for their preparation and to their use as intermediate products for the synthesis of known herbicidally active compounds.

In general terms, α-ketocarboxylic acid amides are valuable intermediate products for the preparation of herbicidally active 1,2,4-triazin-5-one derivatives, which, for example according to DE-OS (German Published Specification) No. 2,165,554, are readily available α-ketocarboxylic acid amides and hydrazine derivatives.

It has already been disclosed that nitriles can be reacted with carboxylic acids or anhydrides thereof in the presence of catalysts, such as mineral acids, to give N-acyl-substituted carboxylic acid amides (see, for example, Compr. Org. Chem. 2, page 539 (1979); "The Chemistry of the Cyano Group", Z.Rappoport, Interscience Publ., New York (1970), pages 239–305; Russ. Chem. Rev. 29, page 331 (1960); and Russ. Chem. Rev. 31, page 615 (1962)).

Thus, for example, the reaction of propionitrile with propionic acid or propionic anhydride in the presence of sulphuric acid leads to dipropionamide in a yield of 28% of theory (see J. Amer. Chem. Soc. 80, page 376 (1958)).

It is also known that diverse secondary reactions can take place during reactions of nitriles with carboxylic acids or carboxylic acid anhydrides in the presence of catalysts. Thus, for example, the reaction of acetonitrile with acetic anhydride in the presence of HCl gas gives the hydrochloride of acetamide and acetyl chloride (Compt. rend. 121, page 1,155 (1895)), while when these components are heated to 200° C., triacetamide is formed.

Under appropriate reaction conditions, an interchange of the radical carrying the nitrile group and the radical carrying the carboxyl group, in the sense of equilibrium reactions, frequently takes place (see Russ. Chem. Rev. 29, page 331 (1960)).

While the preparation of N-acylamides has been described for a number of aliphatic and aromatic nitriles, a corresponding conversion of acyl cyanides to α-ketocarboxylic acid N-acylamides is as yet unknown.

It was hitherto known only that benzoyl cyanide is converted predominantly into acetophenone and other products via C-acylation under particular acylating conditions, with acetic anhydride in the presence of sodium acetate (see Liebigs Ann. Chem. 491, page 264 (1931)).

The present invention now provides, as new compounds, the α-ketocarboxylic acid N-acylamides of the general formula $$R^1-CO-CO-NH-CO-R^2 \quad (I)$$

in which
R$^1$ represents an optionally substituted aliphatic radical with up to 12 carbon atoms, an optionally substituted cycloalkyl radical with 3 to 10 carbon atoms, an optionally substituted phenyl or naphthyl radical or an optionally substituted heterocyclic radical and R$^2$ represents an optionally substituted aliphatic radical with up to 8 carbon atoms or an optionally substituted phenyl radical.

The present invention further provides a process for the preparation of a compound of the invention characterized in that an acyl cyanide of the general formula $$R^1-CO-CN \quad (II)$$

in which R$^1$ has the abovementioned meaning, is reacted with a carboxylic acid anhydride of the general formula $$R^2-CO-O-CO-R^2 \quad (III)$$

in which R$^2$ has the abovementioned meaning, in the presence of a strong acid and optionally in the presence of a solvent, advantageously at a temperature between about −50° and +150° C., and water is then added to the reaction mixture.

If pivaloyl cyanide and acetic anhydride are used as starting substances and the reaction is carried out in the presence of concentrated sulphuric acid, the course of the reaction for the production of compounds of the present invention is illustrated by the following equation:

$$(CH_3)_3C-CO-CN \xrightarrow[(2) H_2O]{(1) (CH_3CO)_2O/H_2SO_4} $$

$$(CH_3)_3C-CO-CO-NH-CO-CH_3$$

Preferred acyl cyanides to be employed as starting substances of formula (II) are those in which R$^1$ represents a straight-chain or branched alkyl radical with 1 to 4 carbon atoms, it being possible for either of these alkyl radicals to be substituted by alkoxy with 1 to 4 carbon atoms, carbalkoxy with 1 to 4 carbon atoms in the alkoxy group, nitro, nitrile and/or halogen (for example fluorine, chlorine, bromine or iodine), represents a cycloalkyl radical which has 3 to 6 carbon atoms in the ring system and is optionally substituted by alkyl, alkoxy or carbalkoxy with in each case up to 4 carbon atoms, nitro, nitrile, and/or halogen (for example fluorine, chlorine and bromine), represents a phenyl or naphthyl radical which is optionally substituted by alkyl, alkoxy or carbalkoxy with in each case up to 4 carbon atoms, nitro and/or halogen (for example fluorine, chlorine and bromine) or represents a 5-membered or 6-membered heterocyclic radical which can contain 1 to 3 hetero-atoms (such as oxygen, sulphur and/or nitrogen) in the ring and can also be fused to a benzene ring, and which is optionally substituted by alkyl, alkoxy or carbalkoxy with in each case up to 4 carbon atoms, nitro, nitrile and/or halogen (for example fluorine, chlorine and bromine). Examples which may be mentioned of heterocyclic radicals which are particularly preferred are: morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

Acyl cyanides of the formula (II) are known and can be prepared by known processes (see Agnew. Chem, 68, pages 425–435 (1965); DE-OS (German Published specifications) Nos. 2,708,182 and 2,708,183, and also U.S. Pat. Nos. 4,284,584 and 4,238,412 and U.S. Pat. No. 4,143,068 which issued Mar. 6, 1979).

Pivaloyl cyanide and benzoyl cyanide may be mentioned as particularly preferred acyl cyanides of formula (II) in the context of this invention.

Preferred carboxylic acid anhydrides to be employed as starting substances of formula (III) are those in which $R^2$ represents an optionally chlorine-substituted alkyl radical with 1 to 4 carbon atoms or a phenyl radical.

The carboxylic acid anhydrides of the formula (III) are available on a large industrial scale in some cases, and they can be prepared by generally known methods, for example from the corresponding carboxylic acids.

Particularly preferred carboxylic acid anhydrides of formula (III) in the context of this invention are propionic anhydride and the anhydrides of the chloroacetic acids, and, especially, acetic anhydride.

The reaction according to the invention is carried out in the presence of a strong acid. Preferred possible strong acids are inorganic acids, such as concentrated sulphuric acid, nitric acid, perchloric acid and phosphoric acid, and also Lewis acids, such as boron trifluoride, aluminum chloride or zinc chloride. Aliphatic and aromatic sulphonic acids and phosphonic acids and halogenoalkanecarboxylic acids, such as trichloroacetic acid, are also suitable. Oxyacids, and in particular concentrated sulphuric acid, are preferably used.

It is possible to carry out the reaction according to the invention in the presence of one or more such acids.

The reaction temperatures can be varied within a substantial range. In general, the reaction is carried out, as indicated above, at temperatures between about $-50°$ and $+150°$ C., preferably between about $0°$ and $100°$ C. Subsequent working up is appropriately carried out by means of ice-water.

The reaction is in general carried out under normal pressure.

The reaction can be carried out in the absence or presence of a solvent or solubilizing agent. Possible solubilizing agents are certain organic solvents; glacial acetic acid and methylene chloride, and also dialkyl ethers, such as diethyl ether or di-iso-propyl ether, and diaryl ethers, such as diphenyl ether, are particularly suitable.

In carrying out the process according to the invention, 0.5 to 10 moles, preferably 0.8 to 4 moles, of carboxylic acid anhydride of the formula (III) are in general employed per mole of acyl cyanide of the formula (II); a molar ratio of acyl cyanide (II) to carboxylic acid anhydride (III) of about 1:1 to 1:2 is particularly preferred.

The acids required for carrying out the process according to the invention are employed in catalytic amounts to amounts greater than the stoichiometric amount. In general, 0.5 to 10 moles, preferably 0.8 to 8 moles and particularly preferably 1 to 4 moles, of acid are employed per mole of acyl cyanide (II).

A molar ratio of carboxylic acid anhydride (III) to acid of about 1:2 is particularly advantageous.

This therefore means that a molar ratio of acyl cyanide (II) to carboxylic acid anhydride (III) to acid of about 1:1:2 to 1:2:4 is very particularly advantageous.

In carrying out the process, it is expedient to follow a procedure in which the acid and carboxylic acid anhydride (III), or a mixture of solvent, acid and carboxylic acid anhydride (III), are initially introduced and the acyl cyanide (II), if appropriate in a solvent, is added.

The reaction times are in general 1 to 10 hours. It is then most expedient to pour the reaction mixture onto ice. The α-ketocarboxylic acid N-acylamides formed can be isolated by filtration or by extraction.

Extraction agents which are suitable for this are solvents which are not miscible with water in all proportions, for example ethers, such as diethyl ether or diisopropyl ether, esters, such as ethyl acetate, ketones, such as methyl isobutyl ketone, halogenated hydrocarbons, such as methylene chloride, chlorobenzene or dichlorobenzene, and also aromatics, such as benzene, toluene, o-xylene, ethylbenzene, cumene or nitrobenzene. Methylene chloride is preferably used.

The α-ketocarboxylic acid N-acylamides of the formula (I) which can be prepared according to the invention are new and they can be used, for example, as intermediate products for the synthesis of herbicidal active compounds. Thus, for example, the particularly herbicidally active compound 4-amino-6-tert.-butyl-3-methylthio-1,2,4-triazin-5(4H)-one, the compound of formula (VI), can be prepared from trimethylpyruvic acid N-acetylamide, the compound of formula (Ia) in accordance with the following equation (see German Patent Specification No. 1,795,784):

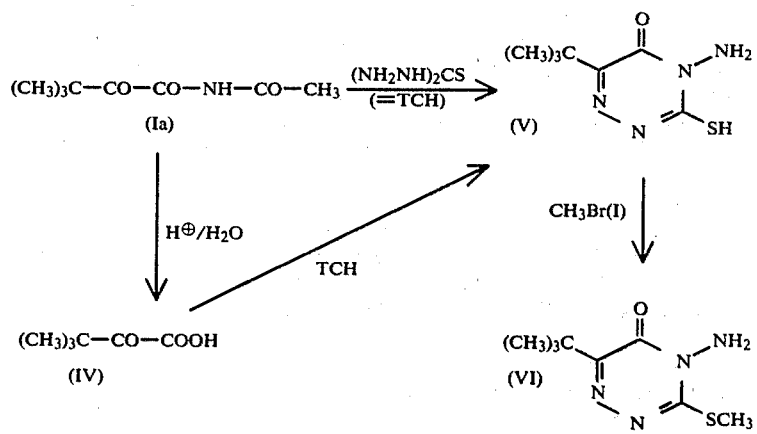

Trimethylpyruvic acid N-acetylamide, the compound of formula (Ia), can be subjected to a condensation reaction, either directly or after prior hydrolysis to the free α-keto-acid of formula (IV) in acid aqueous solution or suspension, with 1 to 1.5 moles of thiocarbohydrazide, $NH_2-NH-CS-NH-NH_2$ (=TCH) at temperatures between $-20°$ and $+150°$ C. to give 4-amino-6-tert.-butyl-3-mercapto-1,2,4-triazin-5(4H)-one, the compound of formula (V), which can be methylated, for example by means of a methyl halide, for example methyl iodide or methyl bromide, in alkaline solution to give the compound of formula (VI) (see Chem. Ber. 97, pages 2,173-8 (1964); DE-OS (German Published Specification) Nos. 2,165,554; 2,460,889; 2,648,300; and U.S. Pat. No. 4,175,188).

The process given here for the preparation of herbicidally active asymmetric triazinones of the type of formula (VI), which proceeds via the new α-ketocarboxylic acid N-acylamides according to the invention, is superior, from an industrial point of view, to the comparable process already known, which proceeds via α-ketocarboxylic acid N-tert.-butylamides (see U.S. Pat. No. 4,175,188 and DE-OS (German Published Specification) No. 2,733,181). In particular, the α-ketocarboxylic acid N-acylamides according to the present invention can be cyclized with thiocarbohydrazide under very mild conditions to give almost quantitative yields of asymmetric triazinones, which are obtained directly in a high purity, while the α-ketocarboxylic acid N-tert.-butylamides which are already known must be heated with thiocarbohriazide to 100° C. for several hours for this reaction, and give yields of only about 70%.

α-Ketocarboxylic acid N-acylamides thus represent a new, valuable class of intermediate products, for example for the synthesis of α-ketocarboxylic acids and of 1,2,4-triazin-5-one derivatives.

The following preparative examples illustrate the invention in more detail.

PREPARATIVE EXAMPLES (A) Preparation of α-ketocarboxylic acid N-acylamides of formula (I)

Example 1

$(CH_3)_3C-CO-CO-NH-CO-CH_3$

First 25.6 g (0.25 mole) of acetic anhydride and then 27.8 g (0.25 mole) of pivaloyl cyanide were introduced, in each case at room temperature, into 49.0 g (0.5 mole) of concentrated sulphuric acid already in the reaction vessel. After subsequently stirring the reaction mixture for 4 hours, 150 g of ice-water were added and the mixture was stirred thoroughly. The reaction product which precipitated was filtered off, washed with 100 ml of water and dried. 37.0 g (86.5% of theory) of trimethylpyruvic acid N-acetylamide were obtained as colorless, glistening flakes of melting point 82° to 84° C.; content according to determination by gas chromatography: >99%. No additional purification operations were required for further reactions.

Analysis: $C_8H_{13}NO_3$ (MW=171.2). Calculated: C 56.13, H 7.65, N 8.18. Found: C 56.10, H 7.85, N 8.30.

EXAMPLE 2

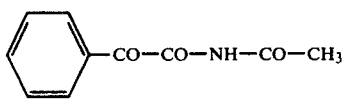

If the procedure followed was analogous to that in Example 1 and benzoyl cyanide was employed instead of pivaloyl cyanide, 38.5 g (79.5% of theory) of phenylglyoxylic acid N-acetylamide were obtained as colorless crystals of melting point 124° to 125° C.; content according to determination by gas chromatography: >99%. No additional purification operations were necessary for further reactions.

Analysis: $C_{10}H_9NO_3$ (MW=191.2). Calculated: C 62.82, H 4.74, N 7.33. Found: C 62.90, H 4.70, N 7.50.

(B) Subsequent reactions

1. Cyclization with thiocarbohydrazide/methylation (a) 4-amino-6-tert.-butyl-3-mercapto-1,2,4-triazin-5(4H)-one, the compound of formula (V)

5.1 g (0.03 mole) of trimethylpyruvic acid N-acetylamide in 20 ml of ethanol were added dropwise to 3.2 g (0.03 mole) of thiocarbohydrazide in 50 ml of 1 N HCl and the reaction mixture was subsequently stirred at room temperature for 5 hours. The product which had precipitated was filtered off, washed with water and dried. 5.7 g of the above product of formula (V) of melting point 210° C. were obtained with a content, determined by gas chromatography, of >99%, which corresponded to a yield of 95% of theory.

(b) 4-Amino-6-tert.-butyl-3-methylthio-1,2,4-triazin-5(4H)-one, the compound of formula (VI)

20 g (0.1 mole) of 4-amino-6-tert.-butyl-3-mercapto-1,2,4-triazin-5(4H)-one, the compound of formula (V), were introduced into a mixture of 97 g of 45% strength sodium hydroxide solution and 65 g of water, while stirring. After all of the product had dissolved, 16.5 g of methyl iodide were added in a manner such that internal temperature did not rise above 30° C. When the addition had ended, the reaction mixture was stirred at room temperature for a further 2 hours. The reaction product which had precipitated was then filtered off, washed with 100 ml of water and dried. 17.3 g (81% of theory) of 4-amino-6-tert.-butyl-3-methylthio-1,2,4-triazin-5-(4H)-one, the compound of formula (VI), of melting point 123° 125° C. were obtained.

2. Hydrolysis of the α-ketocarboxylic acid:

(a) Trimethylpyruvic acid, the compound of formula (IV)

17.1 g (0.1 mole) of trimethylpyruvic acid N-acetylamide (the compound of formula Ia) in 100 ml of 5 N HCl were heated to 90° C. for 4 hours. After cooling, the mixture was extracted by shaking with methylene chloride, the methylene chloride phase was extracted with dilute NaOH solution, the alkaline aqueous solution was adjusted to pH 1 with concentrated HCl and extracted by shaking with ethyl acetate and the ethyl acetate extract was then evaporated. 11.9 g (92% of theory) of trimethylpyruvic acid (the compound of formula IV), were obtained.

(b) Phenylglyoxylic acid $(C_6H_5-CO-COOH)$

The procedure followed is as described in Example B 2. (a), but instead of trimethylpyruvic acid N-acetylamide, the equivalent amount (0.1 mole) of phenylglyoxylic acid N-acetylamide was employed. 13.4 g (89.3% of theory) of phenylglyoxylic acid were obtained.

It will be appreciated that the instant specification and examples are set forth by way of illustration and not limitation, and that various modifications and changes may be made without departing from the spirit and scope of the present invention.

We claim:

1. An α-ketocarboxylic acid N-acylamide of the formula $$R^1—CO—CO—NH—CO—R^2$$

in which
  $R^1$ is an optionally substituted aliphatic radical with up to 12 carbon atoms, an optionally substituted cycloalkyl radical with 3 to 10 carbon atoms, an optionally substituted heterocyclic radical, and
  $R^2$ is an optionally substituted aliphatic radical with up to 8 carbon atoms or an optionally substituted phenyl radical.

2. A compound according to claim 1, in which
  $R^1$ is alkyl with 1 to 4 carbon atoms optionally substituted by alkoxy with 1 to 4 carbon atoms, carbalkoxy with 1 to 4 carbon atoms in the alkoxy group, nitro, nitrile or halogen; cycloalkyl with 3 to 6 carbon atoms optionally substituted by nitro, nitrile, halogen or by alkyl, alkoxy or carbalkoxy each with 1 to 4 carbon atoms in the alkyl group; phenyl or naphthyl optionally substituted by nitro, halogen or by alkyl, alkoxy or carbalkoxy each with 1 to 4 carbon atoms in the alkyl group; or a 5- or 6-membered heterocyclic radical containing 1 to 3 oxygen, sulphur and/or nitrogen ring atoms optionally fused to a benzene ring and optionally substituted by nitro, nitrile, halogen or by alkyl, alkoxy or carbalkoxy each with 1 to 4 carbon atoms in the alkyl group, and
  $R^2$ is alkyl with 1 to 4 carbon atoms optionally substituted by chlorine, or phenyl.

3. A compound according to claim 1, wherein such compound is trimethylpyruvic acid N-acetylamide of the formula $$(CH_3)_3C—CO—CO—NH—CO—CH_3$$

4. A compound according to claim 1, wherein such compound is phenylglyoxylic acid N-acetylamide of the formula

C$_6$H$_5$—CO—CO—NH—CO—CH$_3$

5. A process for the preparation of α-ketocarboxylic acid N-acylamide according to claim 1, comprising reacting an acyl cyanide of the formula $$R^1—CO—CN$$

with a carboxylic acid anhydride of the formula $$R^2—CO—O—CO—R^2$$

in the presence of a strong acid at a temperature between about $-50°$ and $+150°$ C., the molar ratio of the acyl cyanide to the carboxylic acid anhydride being from about 1:0.5 to 1:10, the molar ratio of acid to acyl cyanide being from about 0.5:1 to 10:1 and the molar ratio of carboxylic acid anhydride to acid being about 1:2, and then adding water to the reaction mixture.

6. A process according to claim 5, wherein the reaction is carried out at a temperature between about 0° and 100° C.

7. A process according to claim 5, wherein the reaction is carried out in the presence of a solvent.

8. A process according to claim 5, wherein the molar ratio of the acyl cyanide to the carboxylic acid anhydride is from about 1:0.8 to 1:4.

9. A process according to claim 5, wherein the molar ratio of the acyl cyanide to the carboxylic acid anhydride is from about 1:1 to 1:2.

10. A process according to claim 5, wherein the molar ratio of acid to acyl cyanide is from about 0.8:1 to 8:1.

11. A process according to claim 5, wherein the molar ratio of acid to acyl cyanide is from about 1:1 to 4:1.

12. A process according to claim 5, wherein the molar ratio of acyl cyanide:carboxylic acid anhydride:acid is from about 1:1:2 to 1:2:4.

13. A process according to claim 5, wherein $R^1$ is tert.-butyl or phenyl, and $R^2$ is optionally chlorine substituted alkyl with 1 to 4 carbon atoms, or phenyl.

14. A process according to claim 5, wherein the carboxylic acid anhydride is acetic anhydride and the strong acid is concentrated sulphuric acid.

15. A process according to claim 12, wherein the carboxylic acid anhydride is acetic anhydride and the strong acid is concentrated sulphuric acid, and the reaction is carried out at a temperature between about 0° and 100° C.

* * * * *